（12）United States Patent
Wendelburg

(10) Patent No.: US 10,166,107 B2
(45) Date of Patent: Jan. 1, 2019

(54) FEMORAL STEM AND POST SYSTEM FOR HIP PROSTHESIS

(71) Applicant: Kirk L. Wendelburg, Los Angeles, CA (US)

(72) Inventor: Kirk L. Wendelburg, Los Angeles, CA (US)

( * ) Notice: Subject to any disclaimer, the term of this patent is extended or adjusted under 35 U.S.C. 154(b) by 0 days.

(21) Appl. No.: 15/639,076

(22) Filed: Jun. 30, 2017

(65) Prior Publication Data

US 2017/0296348 A1 Oct. 19, 2017

Related U.S. Application Data

(62) Division of application No. 14/846,509, filed on Sep. 4, 2015, now Pat. No. 9,730,798.

(60) Provisional application No. 62/047,566, filed on Sep. 8, 2014.

(51) Int. Cl.
*A61F 2/36* (2006.01)
*A61B 17/16* (2006.01)
*A61F 2/30* (2006.01)

(52) U.S. Cl.
CPC ........ *A61F 2/3662* (2013.01); *A61B 17/1668* (2013.01); *A61F 2/367* (2013.01); *A61F 2002/30405* (2013.01); *A61F 2002/30774* (2013.01); *A61F 2002/30878* (2013.01); *A61F 2002/3647* (2013.01); *A61F 2002/3684* (2013.01)

(58) Field of Classification Search
CPC .......... A61F 2/36; A61F 2/367; A61F 2/3662; A61F 2002/3627
See application file for complete search history.

(56) References Cited

U.S. PATENT DOCUMENTS

| 6,706,073 | B2 * | 3/2004 | Draenert | ................... | A61F 2/36 |
| | | | | | 623/22.46 |
| 7,179,264 | B2 * | 2/2007 | Cassell | ................ | A61B 17/164 |
| | | | | | 606/92 |

* cited by examiner

*Primary Examiner* — Jason-Dennis Stewart
(74) *Attorney, Agent, or Firm* — Kelly & Kelley, LLP

(57) ABSTRACT

A femoral stem for use in hip replacement surgery, specifically hip replacement surgery in dogs and similar animals but also inclusive to implants used in humans. More particularly, the invention is directed to a femoral stem that includes a lateral bolt or post that protrudes through the cortex or wall of bone opposite the neck of the femoral stem. The lateral bolt or post reduces the occurrence of subsidence in implanted femoral stems. The lateral bolt or post provides an anchor point on the cortex or wall of bone as opposed to relying solely on the compression of the femoral stem against the wall of the bony canal of the femur being implanted.

20 Claims, 9 Drawing Sheets

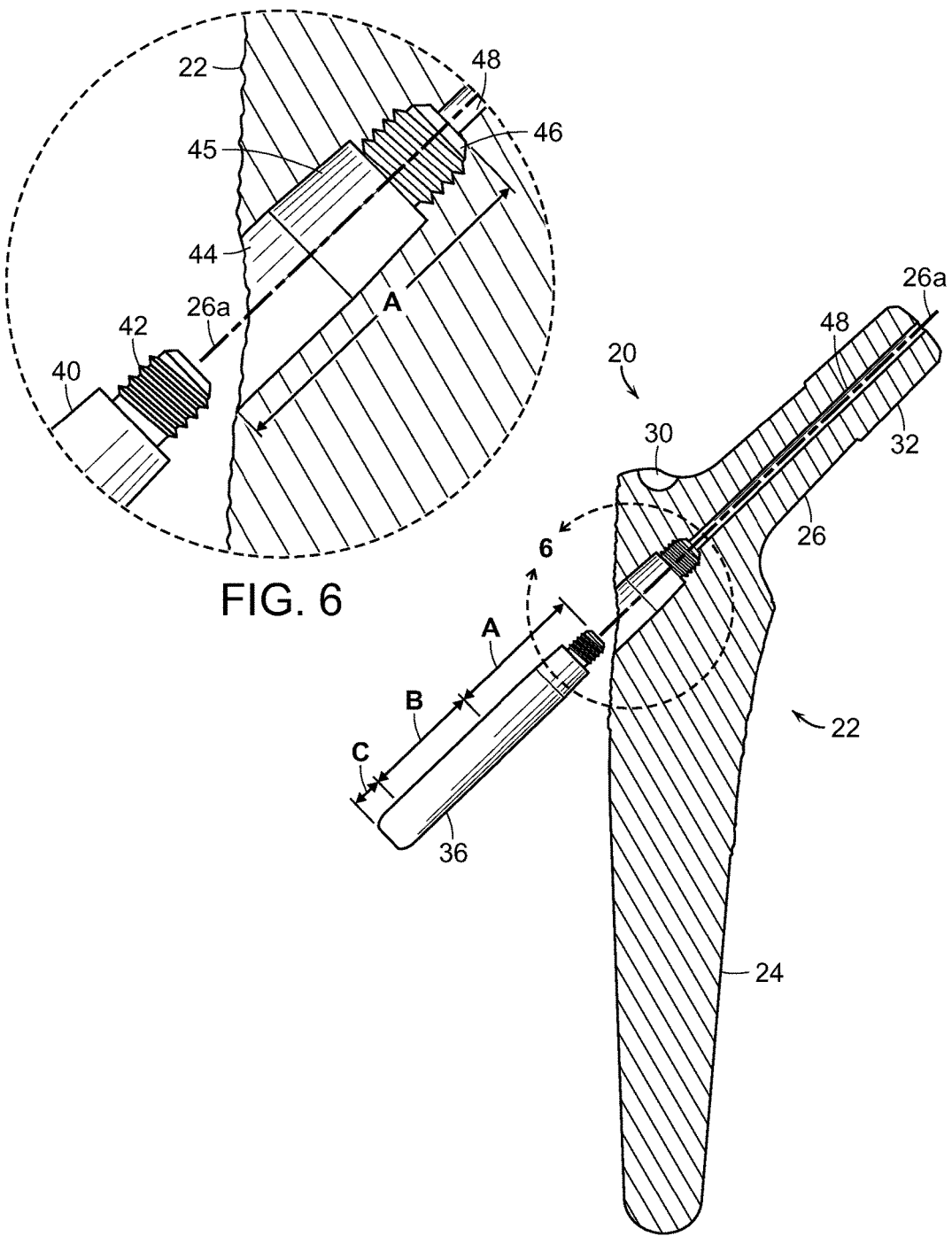

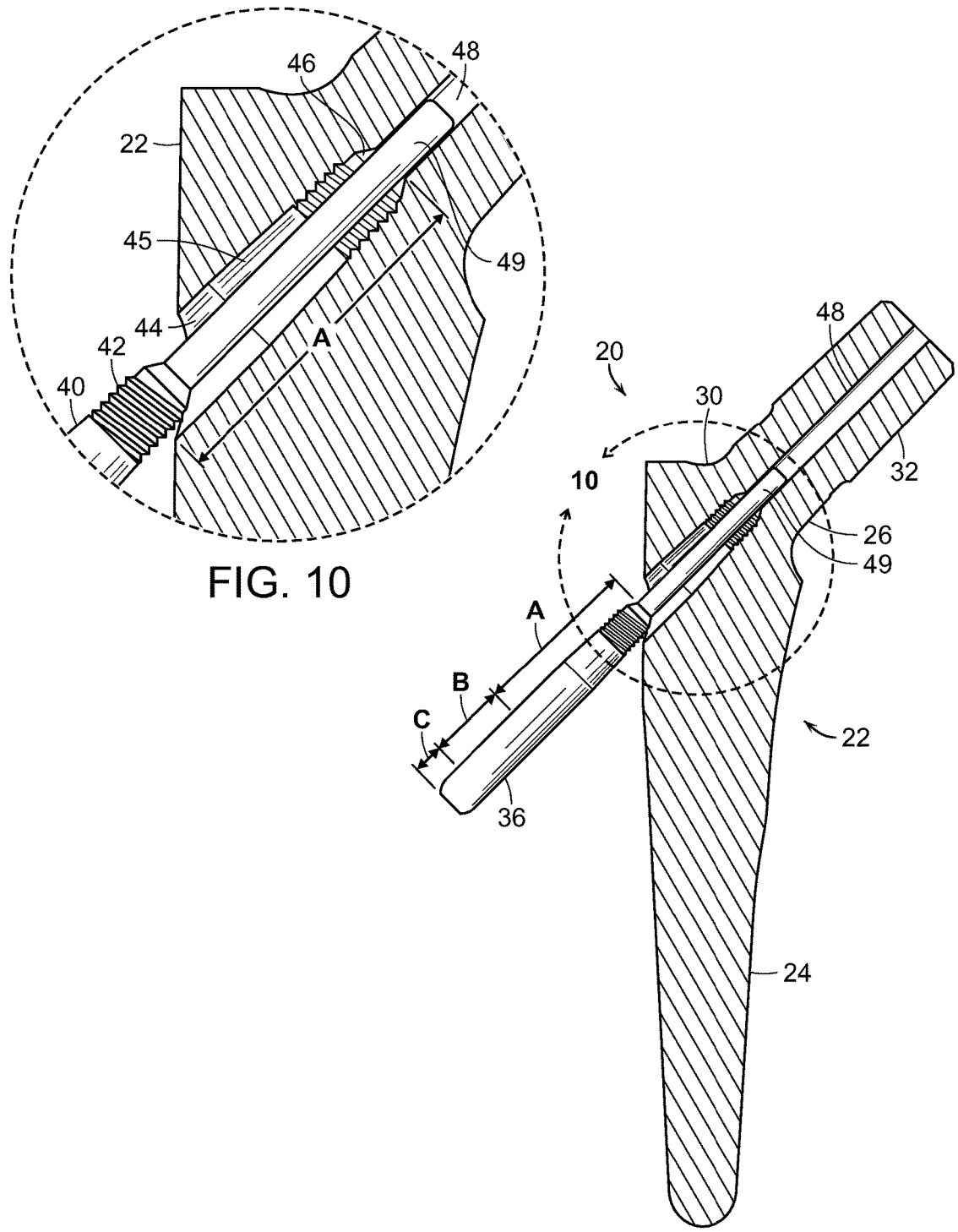

FEMORAL STEM AND POST SYSTEM FOR HIP PROSTHESIS

RELATED APPLICATION

This is a divisional of co-pending U.S. application Ser. No. 14/846,509, filed Sep. 4, 2015, which application claims the benefit of U.S. Provisional Application Ser. No. 62/047,566, filed Sep. 8, 2014.

BACKGROUND OF THE INVENTION

The present invention relates to a femoral stem for hip prosthesis used for replacing the natural joint of a hip joint with an artificial device. More particularly, the invention relates to a modified femoral stem to prevent subsidence.

It is well known that in the orthopaedic field, surgery of the hip joint is generally carried out to treat pathologies such as arthrosis, arthritis, hip luxation, femoral head and neck fractures, or similar conditions generating a progressive wear, pain, or dysfunction of the hip joint. The hip joint connects the femur to the pelvis and comprises the femur head engaged in the acetabulum which is a joint cavity on the outer face of the pelvic bone. In the femur, in addition to said femoral head, there is the neck connecting the head to the femoral body, having a rather longitudinal development.

On the basis of the natural shape of the hip, the prosthesis to be implanted comprises therefore of a femoral part and a pelvic part. The femoral part called a femoral stem is typically made of surgical grade metal, i.e., titanium alloy or stainless steel, and the pelvic part called acetabular cup is typically made of Ultra High Molecular Weight Polyethylene (UHMWP) and/or surgical grade metal, i.e., titanium alloy or stainless steel. The femoral stem comprises a main body also known as the stem, which is implanted into a longitudinal cavity of bone made in the natural femoral shaft. The acetabular cup is implanted into the bony bed made in the natural pelvic acetabulum. Such femoral stem ends at the top of the natural femoral shaft with a shoulder which blends into a femoral neck projecting from the shoulder and having a terminal cone. A spherical femoral head also made of metal or ceramics is inserted on to the above mentioned terminal cone and forms the pivot ball of the artificial ball and socket joint after placing it into the acetabular cup.

The surgical operation to the patient's hip begins with cutting the femoral neck to remove the femoral head and neck. Such operation is called a femoral neck resection or osteotomy. The resected natural femoral head and neck are removed to expose the top of the femoral canal. Subsequent preparation of the femur by proper pins, drills, and rasps prepares the internal canal of the femoral bone where the prosthetic stem will be inserted. The acetabulum is then prepared by removing cartilage and bone with spherical mill to form a seat into which the acetabular cup is then inserted. The femoral stem is then inserted into the prepared femoral canal. A spherical head is placed onto the terminal cone of the femoral prosthesis neck. After the femoral stem and head are assembled, the head is reduced into the implanted acetabular cup restoring the original configuration of the hip joint.

Once implanted, the femoral prosthesis and the acetabular cup recreate almost identically the original shape and function of the hip joint. Such provides pain relief and recovery of the joint function so as to allow the patient to have a normal life for many years.

The stem is anchored in the femur through three main methods. The first consisting of solidification of a liquid polymer around the stem that acts as a cement, connecting stem firmly to the bone. Most modern methods use a natural process whereby the femoral stem is press fit or compressed into the bony bed of the femoral canal. The direct contact of bone to stem allows for bone integration into the metal of the stem. The anchoring ability of the bone growth into the metal implant is enhanced by a roughened or textured outer surface of the metal. The final and less common method of stem fixation uses several screws that anchor the stem to the wall of the femoral canal.

One major disadvantage of press fit bony ingrowth method is subsidence. Subsidence is the progressive post-operative movement or migration of the implanted femoral stem down the bony canal of the femoral shaft. In certain patients, particularly active patients or animals that cannot understand instructions to minimize activity, the femoral stem may be impacted further into the femur prior to bony integration through repeated impacts from normal activity. Subsidence may result in: 1) a decreased ability of the bone to grow into the metal surface resulting in a loose femoral stem, 2) a significant change in position of the stem resulting in an increased incidence of dislocation of the femoral head out of the cup, and 3) fracturing of the femoral shaft as the implant gets pushed down the canal. Fracturing or breaking of the femur bone particularly in non-human patients, such as dogs or cats may be due to the thinner bone cortical walls of the bones compared to humans.

The present invention addresses these needs and provides other related advantages.

SUMMARY OF THE INVENTION

The present invention is directed to a femoral stem for a hip joint prosthesis. The femoral stem has a femoral base with a generally elongated shape having a proximal end and a distal end. The femoral stem also has a femoral neck with a generally tubular shape extending from the proximal end of the femoral base and having a concentric axis. A lateral port is on a side of the femoral base generally opposite the femoral neck and in alignment with the concentric axis. The femoral stem also has a lateral post with a first end removably secured within the lateral port and a second end extending a predetermined distance from the side of the femoral base.

The femoral base preferably has a longitudinal axis along the elongated shape with the longitudinal axis and the concentric axis form an operating angle therebetween. The operating angle may be between 30 degrees and 60 degrees, preferably approximately 45 degrees.

The femoral neck preferably includes a guide hole passing concentrically through the femoral neck along the central axis. The guide hole preferably connects to the lateral port. The lateral post preferably includes a guide rod extending from the first end of the lateral post in alignment with a long axis of the lateral post. The guide rod preferably has an outer diameter substantially equal to an inner diameter of the guide hole, such that the guide rod snugly but easily slides through the guide hole.

The predetermined distance from the side of the femoral base is such that when the lateral post is secured within the lateral port, the second end thereof extends approximately 2 mm beyond a lateral cortex of a femur bone into which the femoral stem is implanted.

A process for implanting a lateral stem as described above begins with preparing an end of a femur bone for implantation of the femoral stem. The femoral stem preferably includes a femoral neck that replicates a neck on a femur bone of a patient, wherein the femoral stem has a lateral port on a side generally opposite the femoral neck in-line with a concentric axis of the femoral neck. The femoral stem is then implanted in the prepared femur bone. A lateral hole is drilled through a lateral cortex of the femur bone adjacent to the lateral port on the femoral stem. The lateral post is then installed through the lateral hole and into the lateral port such that a portion of the lateral post protrudes from the lateral cortex of the femur bone.

In this process, the preparing step may include exposing a hip joint of a patient comprising a femur bone connected to a hip socket. The femur bone is separated from the hip socket and a head and neck of the femur bone is cut off so as to expose an interior of the femur bone. The exposed interior of the femur bone is rasped out to create a cavity for receiving the femoral stem.

The drilling step may include inserting a first drill bit through the guide hole along the concentric axis of the femoral neck and through the lateral port to contact the femur bone adjacent to the lateral port. A pilot hole is drilled through the lateral cortex of the femur bone using the first drill bit, where the pilot hole is aligned with the lateral port and the concentric axis. A guide wire is inserted through the guide hole, the lateral port, and the pilot hole in the lateral cortex such that the guide wire protrudes from the femur bone. A second drill bit is aligned with the guide wire protruding from the pilot hole. The lateral hole is drilled through the lateral cortex using the second drill bit in-line with the concentric axis of the femoral neck. The first drill bit is preferably a pilot hole drill bit on the order of about 1.5 mm. The second drill bit is a preferably cannulated drill bit to fit over the guide wire. The process may further include cleaning the lateral port and lateral hole after the drilling step to remove any bone debris.

The lateral post is preferably secured within the lateral port, as by screw threads or a comparable securing mechanism. The implanting step may include inserting the femoral stem into the cavity in the prepared end of the femur bone and impacting the femoral stem into the cavity.

The process may further include measuring a depth of the lateral hole and selecting the lateral post based upon the measured depth of the lateral hole such that the lateral post protrudes from the lateral cortex by at least 2 mm.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 5 is an exploded, partial cross-sectional view of a femoral stem with lateral post;

FIG. 6 is a close-up view of the femoral stem with lateral post of FIG. 5 designated by circle 6;

FIG. 9 is an exploded, partial cross-sectional view of an alternate embodiment of a femoral stem with lateral post; and FIG. 10 is a close-up view of the alternate embodiment of the femoral stem with lateral post of FIG. 9 designated by circle 10.

DETAILED DESCRIPTION OF THE PREFERRED EMBODIMENTS

Figure 1A:
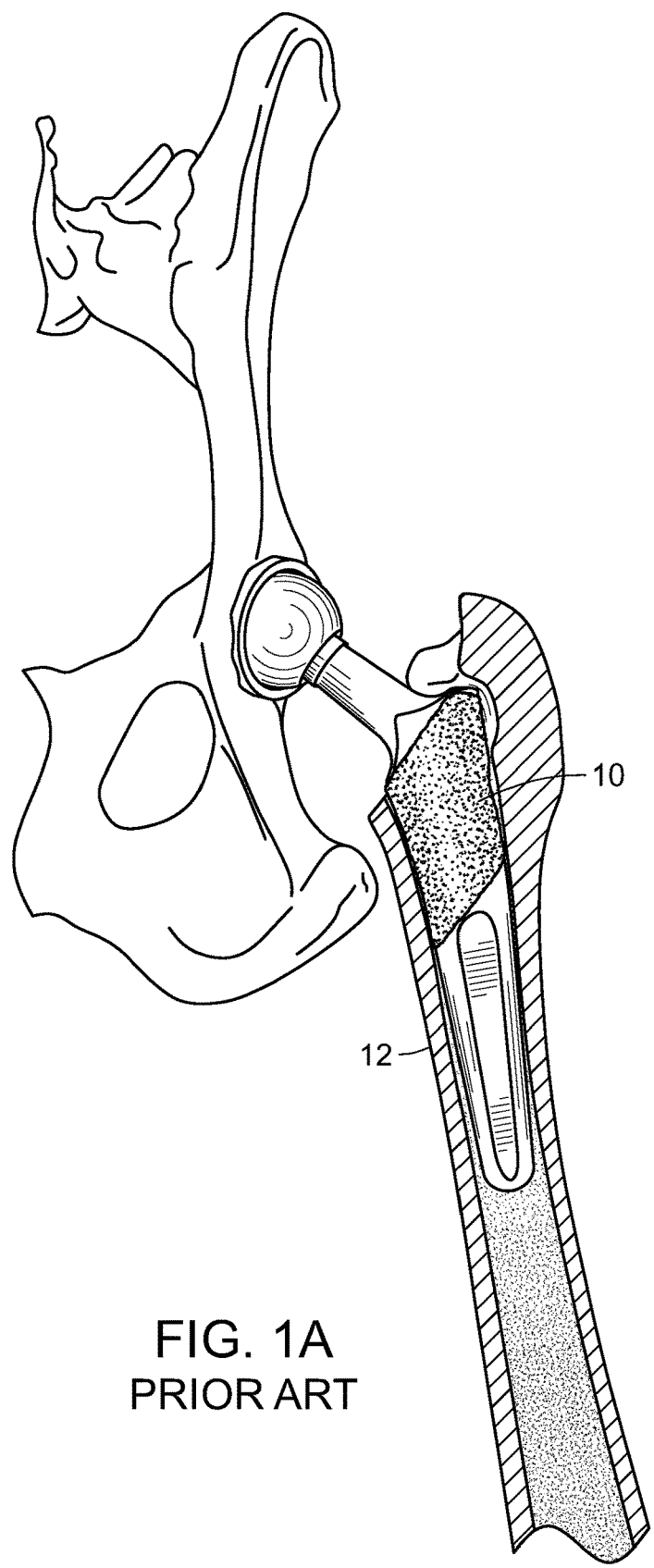
FIG. 1A is an environmental, partial cut-away of a prior art femoral stem implanted as part of prosthesis in a canine.
Figure 1B:
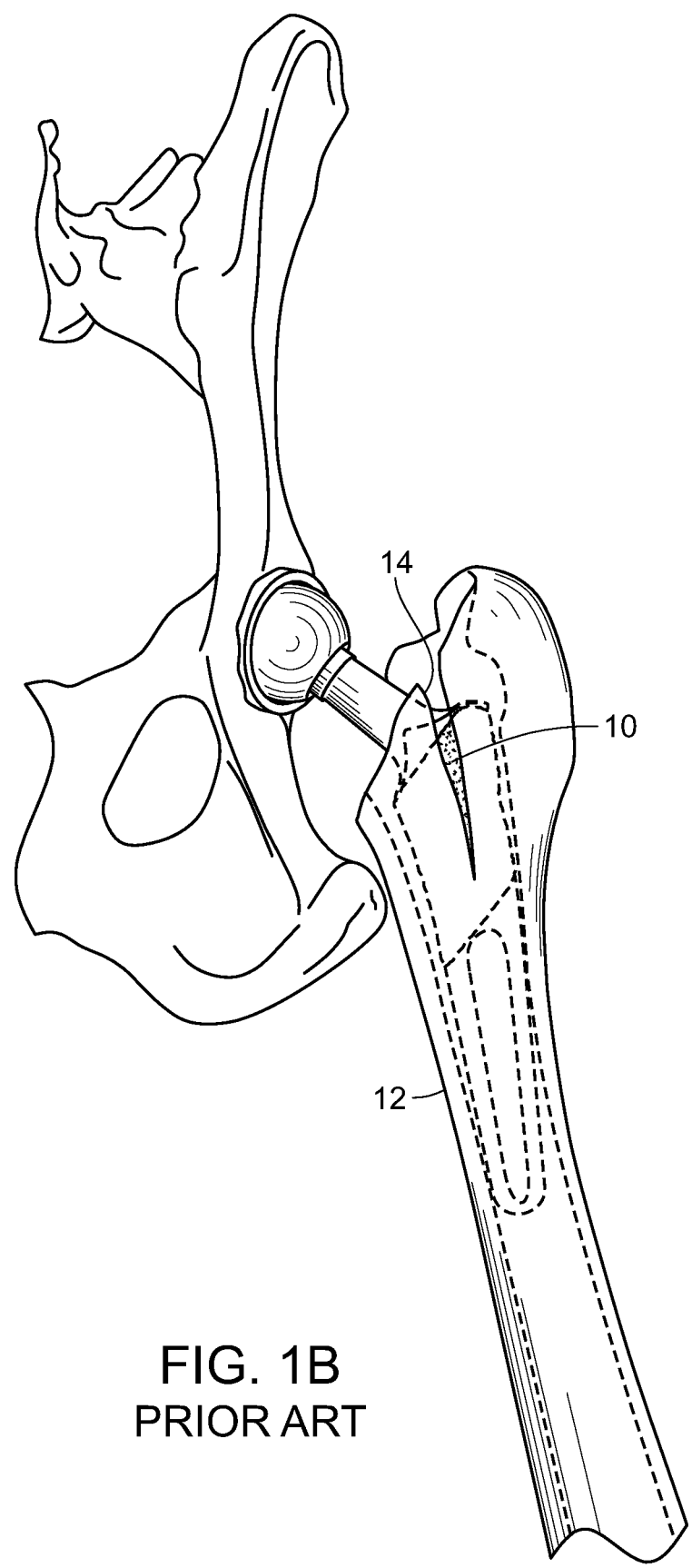
FIG. 1B is the femoral stem of FIG. 1A after subsidence and resulting fracture of the femoral bone.
Figure 2:
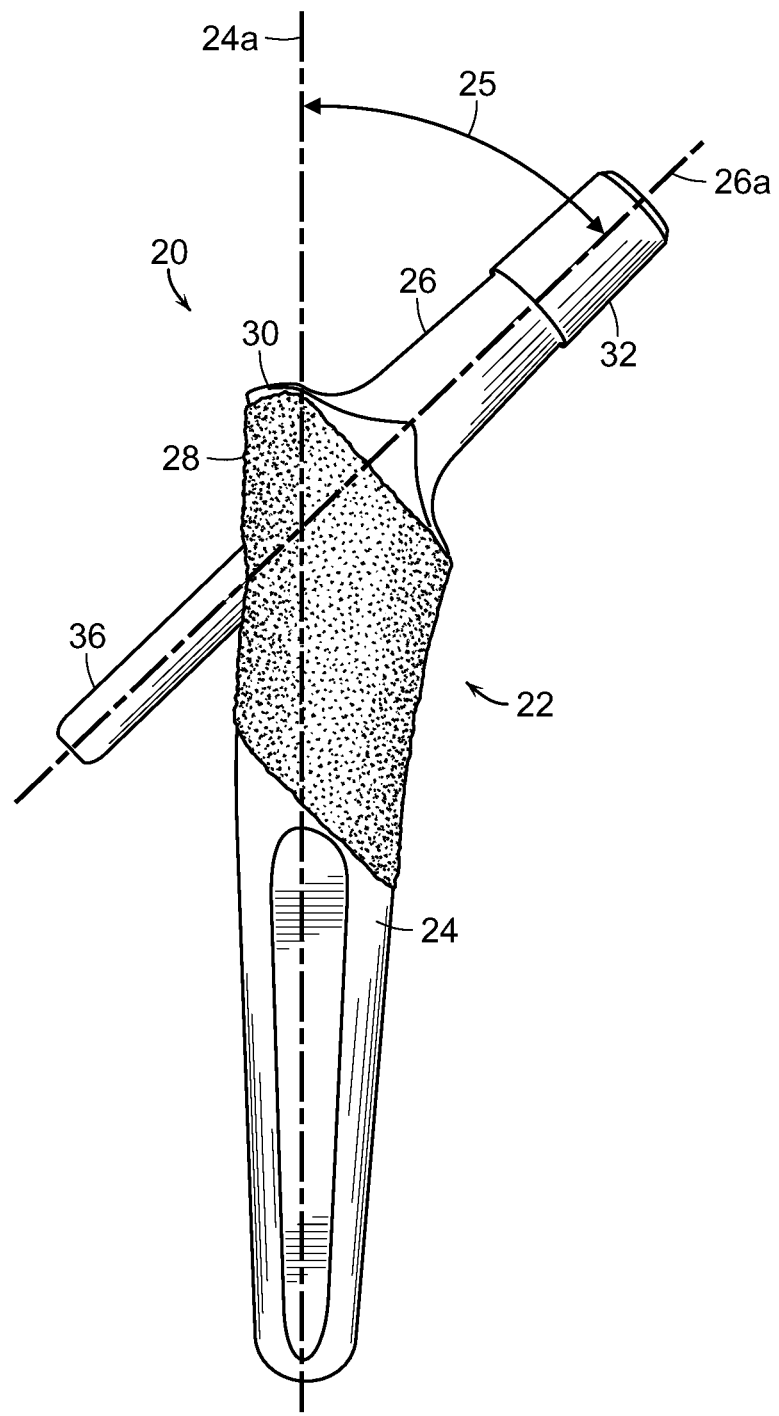
FIG. 2 is a plan view of a femoral stem with lateral post.
Figure 3:
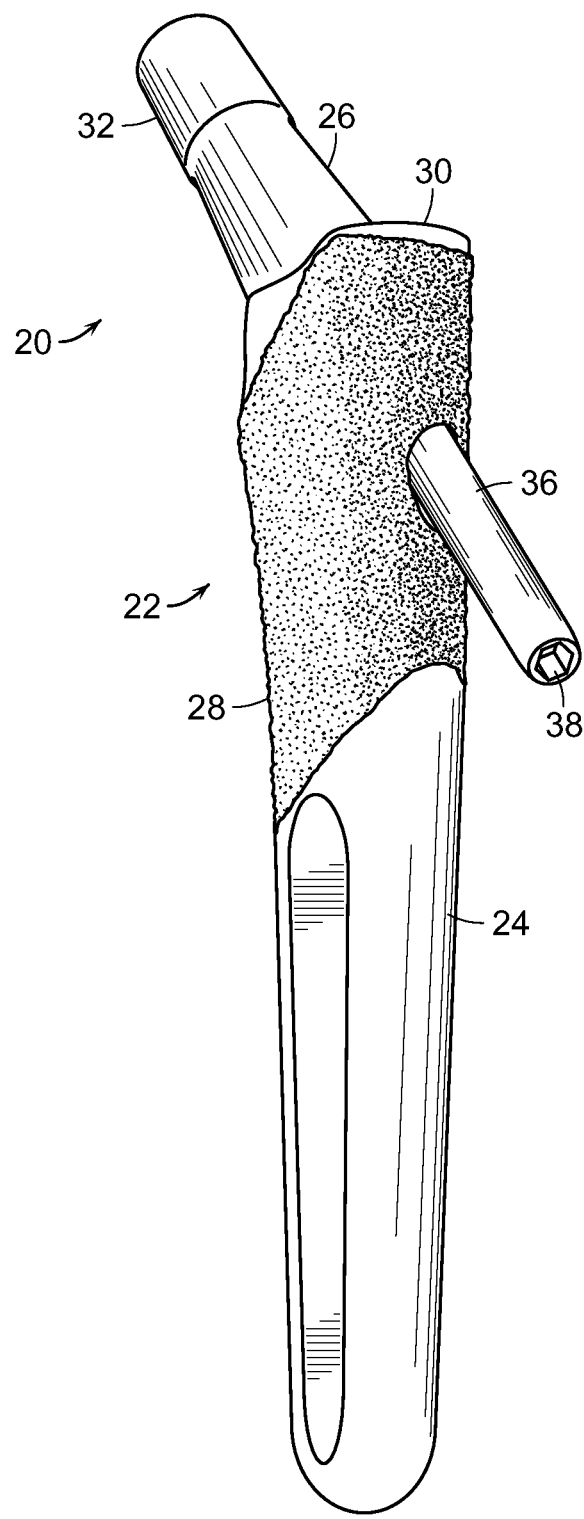
FIG. 3 is a perspective view of a femoral stem with lateral post.

FIGS. 1A and 1B illustrate a prior art femoral stem 10 implanted as part of a hip prosthesis in a canine. FIG. 1A illustrates the femoral stem 10 implanted in the femur bone 12 at its normal and intended depth. FIG. 1B illustrates the femoral stem 10 after subsidence, i.e., after the stem 10 has moved deeper into the femur bone 12. The subsidence has resulted in fractures 14 of the femur bone 12. Such fractures 14 are more frequently seen in canine bones because they tend to be thinner and more fragile than human femur bones.

In the accompanying FIGS. 2-8, the femoral stem with lateral post system of the present invention, which has application for use in canine, human, or other medical uses, will be generally referred to by reference numeral 20. The femoral stem 22 may be constructed in a manner similar to almost any other prior art stem. The stem 22 preferably includes a base portion 24, a neck 26, and a roughened surface 28 to provide for ingrowth of bone. The base 24 has a longitudinal axis 24a. The neck 26 also has a longitudinal axis 26a. Preferably, the base 24 and neck 26 are configured such that the base longitudinal axis 24a and neck longitudinal axis 26a form an offset angle 25 that replicates the original angle of the femur neck and head relative to the vertical axis of the femur body, which varies from species to species. For canines, this offset angle 25 varies between 20° and 50° depending upon the original orientation of the patient's femur. For humans, this offset angle 25 varies between 30° and 60° depending upon the original orientation of the patient's femur. Other offset angles may be appropriate for other species of animals. The neck 26 preferably includes a tip 32 for receiving a spherical head 34 during implantation also as described below.

The lateral post 36 has a generally cylindrical construction and protrudes from a side of the stem 22 opposite the neck 26. As described below, the post 36 is a lateral cortical post to provide the desired support. The lateral post 36 is disposed in alignment with the longitudinal axis 26a of the neck 26. The exposed end of the lateral post 36 preferably has a socket 38 or similar structure to allow for manipulation, i.e., rotating or turning, of the post 36. The socket 38 may be configured to receive a hex wrench or similar tool. As described further below, this is useful in insertion and removal of the post 36 through a threaded connection.

Figure 4:
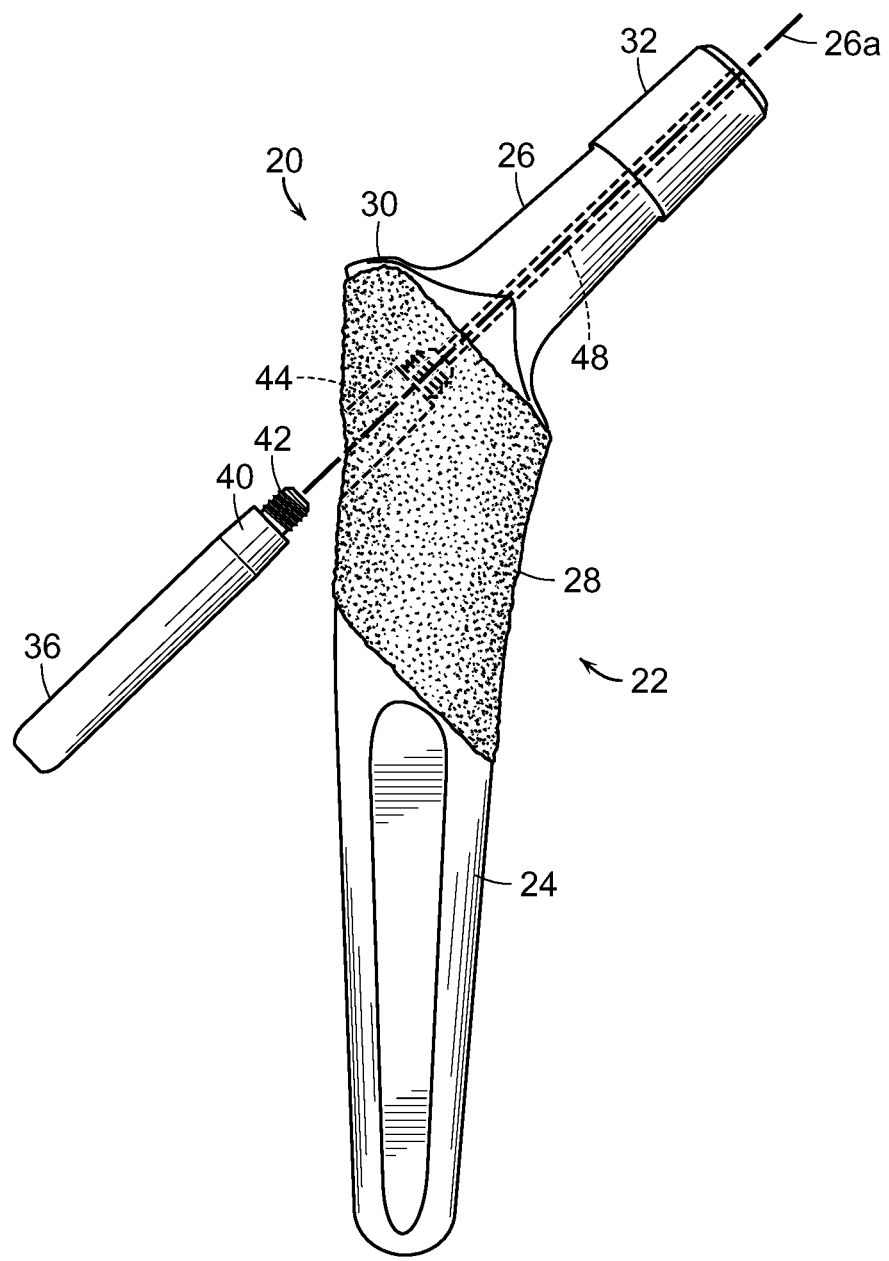
FIG. 4 is a partially exploded plan view of a femoral stem with lateral post.

FIGS. 4-6 illustrate the connection of the post 36 to the stem 22. Opposite the socket 38, the post 36 has an insertion tip 40 where the generally cylindrical body of the post 36 tapers slightly. A connection structure 42, i.e., a threaded tip, is disposed on the end of the tapered insertion tip 40. The stem 22 includes a port 44 configured to receive the insertion tip 40 of the post 36. The port 44 preferably has a slight taper 45 to match the taper of the insertion tip 40. The deepest end of the port 44 includes a mating connection structure 46, i.e., a threaded hole. The stem 22 further includes a guide hole 48 that passes through the center of the neck 26 and out the port 44. This guide hole 48 is useful in the implantation procedure described below.

During implantation, the typical procedure for implanting a stem 22 into a femur bone 12, e.g., cutting the head and neck off the femur and rasping out a cavity, is followed. Once the bone 12 is cut and rasped out as necessary, the stem 22 is impacted into the femur bone 12 using the appropriate tools, e.g., a hammer, and impact point 30. Before the spherical head 34 is attached to the tip 32 of the neck 26, a surgeon must drill a hole through the lateral bone of the femur to access the port 44. For proper alignment of the post 36, one must determine where the port 44 is behind the femoral bone.

Rather than drill through the muscle and bone to the port 44, proper alignment is achieved by drilling a pilot hole through the guide hole 48 from the tip of the neck through the port 44, then out through the lateral bone of the femur. In a particularly preferred embodiment, the surgeon uses a 1.5 mm drill bit or similarly sized tool to create the properly aligned access to the port 44 through the lateral bone of the femur. A K-wire is then inserted through the guide hole and out the freshly drilled opening, e.g., pilot hole, with any excess K-wire cut off at the neck tip. The tip of the K-wire preferably protrudes through the lateral femoral bone by approximately 1 to 2 cm.

The surgeon then uses a power drill with a cannulated drill bit over the K-wire as a guide to drill a sufficiently sized hole, i.e. 4.5 mm, back through the lateral bone to the port 44. It is preferable that the power drill is not used to drill down to the implant to avoid damaging the port 44, the stem 22, or otherwise move or vibrate the stem 22 within the bone. A hand drill with a similarly sized drill bit can be used to remove the small amount of cancellous bone adjacent to the implant.

The port 44 and hole are cleaned or flushed out to remove any bone or other debris. A depth gauge is then used to measure for proper length of the post 36 from the outer bone layer, e.g., lateral cortex 50, to the side wall of the stem 22 at the opening of the port 44. The post 36 must be sufficiently long such that it protrudes through the cortex of the bone to benefit from the support of the outer bone layer. Conversely, the post 36 should not protrude through the cortex of the bone so much that it interferes with normal function of the hip joint and leg muscles or otherwise cause discomfort.

With the proper length of the post 36 determined, the post is inserted through the newly drilled hole in the lateral femoral bone to the port 44. The threads 42 of the insertion tip 40 enter the port 44 where the connection structures 42, 46 comprise mated threaded connections. The post 36 is screwed into the port 44 until a sufficiently strong and secure connection is created by the metal to metal bond of the tapered metal 40 and 45. Preferably, the surgeon uses a tool, i.e., a hex wrench, in the socket 38 to ensure a proper connection. In addition, the connection structure 42 and mating connection structure 46 are joined to forcefully pull the tapers 40 and 45 together in the port 44.

Figure 7:
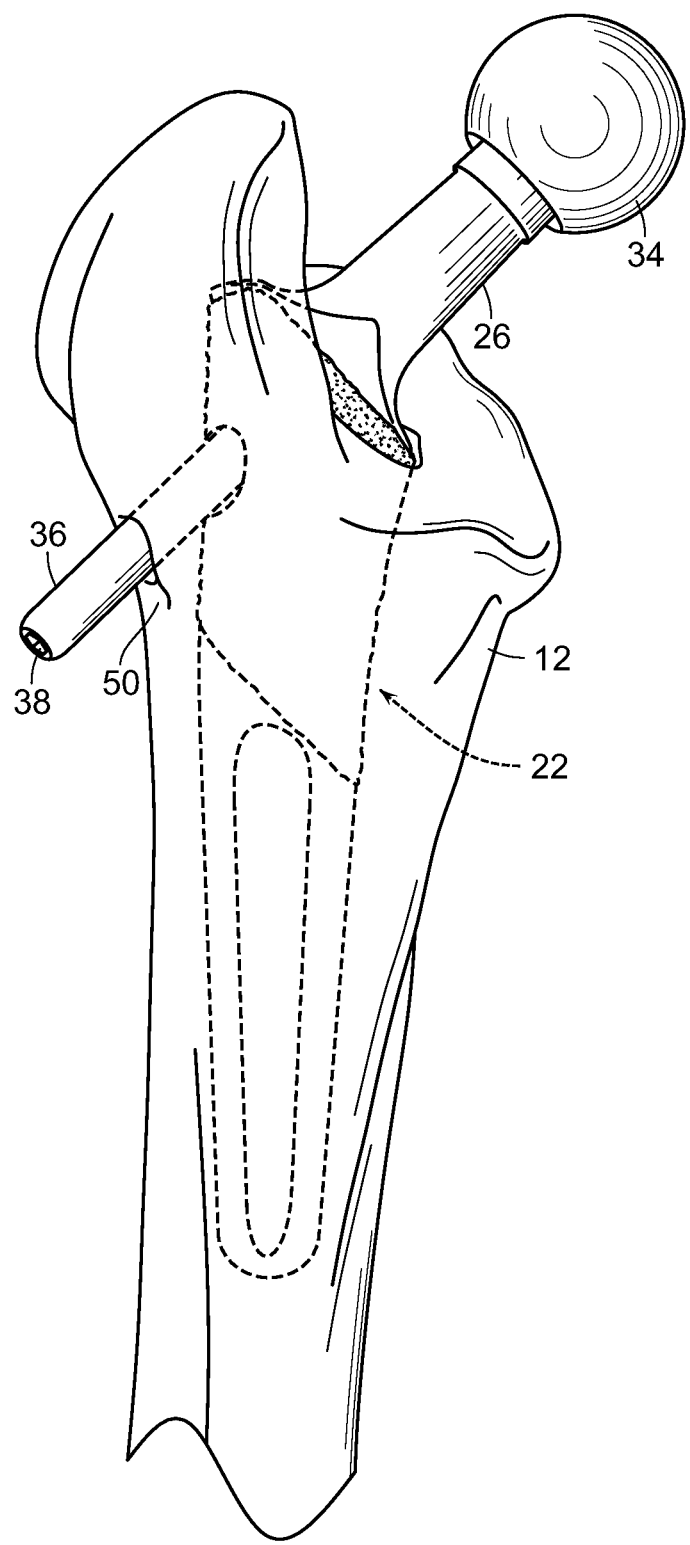
FIG. 7 is a transparent, environmental view of a femoral stem with later post inserted into a femur bone.
Figure 8:
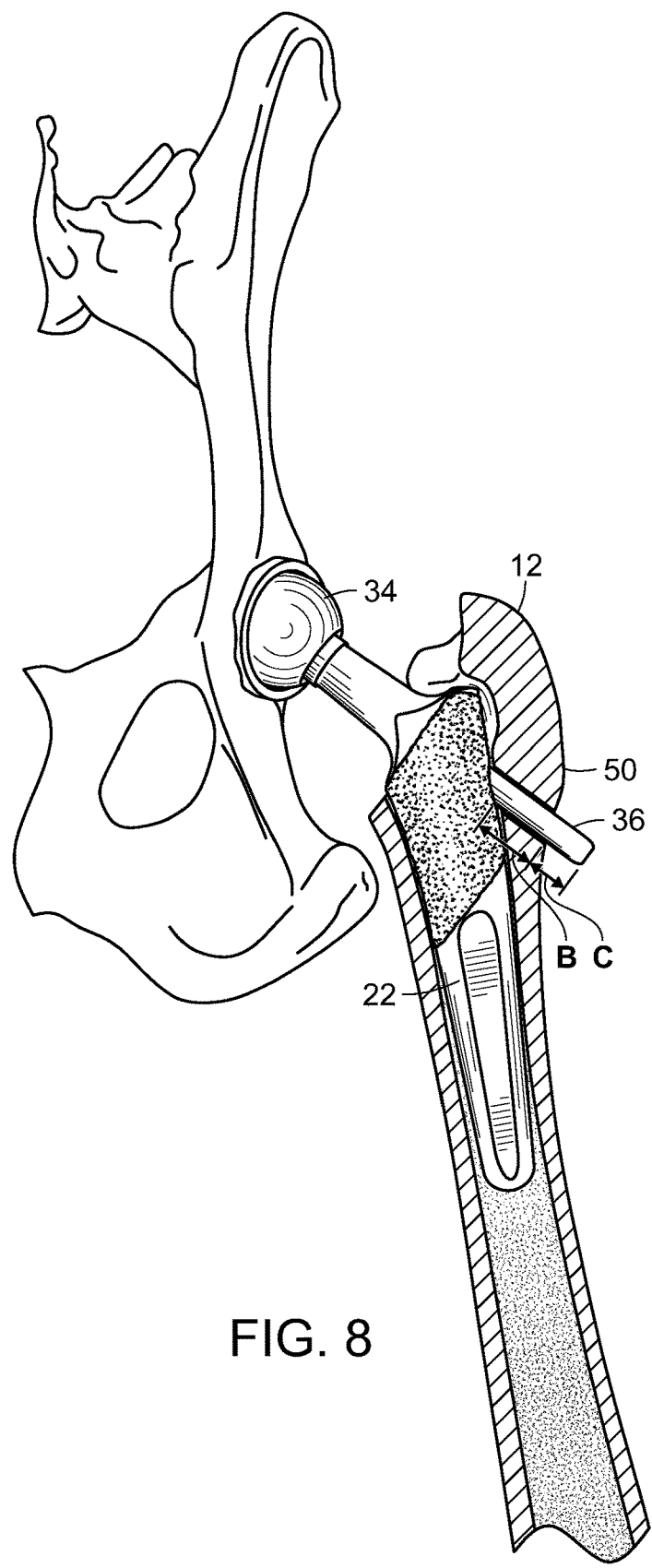
FIG. 8 is an environmental, partial cut-away of a femoral stem with lateral post implanted as part of a prosthesis in a canine.

FIGS. 7 and 8 illustrate the stem and post system 20 implanted in a canine femur bone 12, with the post 36 protruding through the lateral cortex 50 of the femoral bone 12. Both of these illustrations demonstrate how the post 36 provides an anchor in a thickened area of the bone to prevent or reduce the occurrence of subsidence.

FIGS. 9 and 10 illustrate an alternate embodiment of the femoral stem with lateral post described above. In this alternate embodiment, the lateral post 36 includes an extension guide post 49 extending beyond the threaded connection 42 thereof. The extension guide rod 49 is preferably perfectly aligned with a longitudinal axis of the lateral post 36. The diameter of the extension guide rod 49 preferably closely matches the inner diameter of the guide hole 48 while still allowing the extension guide rod 49 to pass through the guide hole 48 with minimal resistance. The purpose of the extension guide rod 49 is to assist a user in properly aligning the lateral post 36 within the port 44 so that the connection structure 42 and mating connection structure 46 are properly aligned. In the case where these mating connection structures are threads, this proper alignment helps to minimize cross-threading during implantation.

FIGS. 9 and 10 further illustrate various length measurements of the port 44 and post 36. As shown in FIGS. 9 and 10, distance A measures the longest longitudinal dimension of port 44 and also corresponds to a portion of the post 36. Distance A will be a fixed distance depending upon the size of the femoral stem for a particular patient. This corresponding portion of the post 36 spans from the tip of the connection structure 42, which is also the point at which the extension guide rod 49 is attached, to an approximate midpoint of the post 36 corresponding to the longest longitudinal dimension of the port 44. Distance B represents the distance from the opening of the port 44, e.g., side wall of the stem 22, to the exterior surface of the femur, i.e., the lateral cortex 50. This distance B is also illustrated in FIG. 8. As will be understood by those skilled in the art, the distance B will vary depending upon the size of the femur bone 12 which varies from patient-to-patient depending upon factors such as species, maturity, and other factors. The distance B is determined by using the depth gauge as described above. The distance C represents that portion of the post 36 that protrudes from the lateral cortex 50 of the femoral bone 12—the distance from the side wall of the femur 12 to the exposed end of the post 36. This distance C must extend through the lateral cortex 50 sufficient to provide the strength of the lateral cortex to the anti-subsidence function of the post 36. In a particularly preferred embodiment, the distance C is at least two millimeters. This distance C is also shown in FIG. 8.

Although several embodiments have been described in detail for purposes of illustration, various modifications may be made without departing from the scope and spirit of the invention. Accordingly, the invention is not to be limited, except as by the appended claims.

What is claimed is:

1. A process for implanting a femoral stem for a hip joint prosthesis, comprising a femoral base having a generally elongated shape with a proximal end and a distal end, a femoral neck having a generally tubular shape extending from the proximal end of the femoral base and having a concentric axis, a lateral port on a side of the femoral base generally opposite the femoral neck and in line with the concentric axis, and a lateral post having a first end removably secured within the lateral port and a second end extending a predetermined distance from the side of the femoral base, comprising the steps of:

preparing an end of a femur bone for implantation of the femoral stem;
  implanting the femoral base in the femur bone;
  drilling a lateral hole through a lateral cortex of the femur bone adjacent to the lateral port on the femoral stem;
  measuring a depth of the lateral hole;

selecting the lateral post based upon the measured depth of the lateral hole such that the lateral post protrudes from the lateral cortex by at least 2 mm; and installing the lateral post through the lateral hole and into the lateral port such that a portion of the lateral post protrudes from the lateral cortex of the femur bone.

2. The process of claim 1, wherein the preparing step comprises the steps of:

exposing a hip joint of a patient comprising a femur bone connected to a hip socket;

separating the femur bone from the hip socket;

cutting off a head and neck of the femur bone so as to expose an interior of the femur bone; and rasping out the exposed interior of the femur bone to create a cavity for receiving the femoral stem.

3. The process of claim 1, wherein the drilling step comprises the steps of:

inserting a first drill bit through a guide hole along the concentric axis of the femoral neck and through the lateral port to contact the femur bone adjacent to the lateral port;

drilling a pilot hole through the lateral cortex of the femur bone using the first drill bit, wherein the pilot hole is aligned with the lateral port and the concentric axis;

inserting a guide wire through the guide hole, the lateral port, and the pilot hole in the lateral cortex such that the guide wire protrudes from the femur bone;

aligning a second drill bit with the guide wire protruding from the pilot hole; and drilling the lateral hole through the lateral cortex using the second drill bit in-line with the concentric axis of the femoral neck.

4. The process of claim 1, further comprising the step of securing the lateral post in the lateral port.

5. The process of claim 4, wherein the securing step comprises screwing the lateral post into the lateral port.

6. The process of claim 1, wherein the implanting step comprises the steps of:

inserting the femoral stem into a cavity in the prepared end of the femur bone;

impacting the femoral stem into the cavity.

7. The process of claim 1, further comprising the step of cleaning the lateral port and lateral hole after the drilling step to remove any bone debris.

8. A process for implanting a femoral stem of a hip joint prosthesis, comprising the steps of:

providing a femoral stem having a femoral neck that replicates a neck on a femur bone of a patient, wherein the femoral stem has a lateral port on a side generally opposite the femoral neck in-line with a concentric axis of the femoral neck;

preparing an end of the femur bone for implantation of the femoral stem;

implanting the femoral stem in the femur bone;

drilling a lateral hole through a lateral cortex of the femur bone adjacent to the lateral port on the femoral stem;

measuring a depth of the lateral hole;

selecting the lateral post based upon the measured depth of the lateral hole such that the lateral post protrudes from the lateral cortex by at least 2 mm; and installing a lateral post through the lateral hole and into the lateral port such that a portion of the lateral post protrudes from the lateral cortex of the femur bone.

9. The process of claim 8, wherein the preparing step comprises the steps of:

exposing a hip joint of a patient comprising a femur bone connected to a hip socket;

separating the femur bone from the hip socket;

cutting off a head and neck of the femur bone so as to expose an interior of the femur bone; and rasping out the exposed interior of the femur bone to create a cavity for receiving the femoral stem.

10. The process of claim 8, further comprising the step of securing the lateral post in the lateral port.

11. The process of claim 10, wherein the securing step comprises screwing the lateral post into the lateral port.

12. The process of claim 8, wherein the implanting step comprises the steps of:

inserting the femoral stem into a cavity in the prepared end of the femur bone;

impacting the femoral stem into the cavity.

13. The process of claim 8, further comprising the step of cleaning the lateral port and lateral hole after the drilling step to remove any bone debris.

14. A process for implanting a femoral stem of a hip joint prosthesis, comprising the steps of:

providing a femoral stem having a femoral neck that replicates a neck on a femur bone of a patient, wherein the femoral stem has a lateral port on a side generally opposite the femoral neck in-line with a concentric axis of the femoral neck;

preparing an end of the femur bone for implantation of the femoral stem;

implanting the femoral stem in the femur bone;

inserting a first drill bit through a guide hole along the concentric axis of the femoral neck and through the lateral port to contact the femur bone adjacent to the lateral port;

drilling a pilot hole through a lateral cortex of the femur bone using the first drill bit, wherein the pilot hole is aligned with the lateral port and the concentric axis;

inserting a guide wire through the guide hole, the lateral port, and the pilot hole in the lateral cortex such that the guide wire protrudes from the femur bone;

aligning a second drill bit with the guide wire protruding from the pilot hole;

drilling a lateral hole through the lateral cortex adjacent to the lateral port using the second drill bit in-line with the concentric axis of the femoral neck; and installing a lateral post through the lateral hole and into the lateral port such that a portion of the lateral post protrudes from the lateral cortex of the femur bone.

15. The process of claim 14, wherein the first drill bit is a pilot hole drill bit and the second drill bit is a cannulated drill bit.

16. The process of claim 14, wherein the preparing step comprises the steps of:

exposing a hip joint of a patient comprising a femur bone connected to a hip socket;

separating the femur bone from the hip socket;

cutting off a head and neck of the femur bone so as to expose an interior of the femur bone; and rasping out the exposed interior of the femur bone to create a cavity for receiving the femoral stem.

17. The process of claim 14, further comprising the step of securing the lateral post in the lateral port.

18. The process of claim 17, wherein the securing step comprises screwing the lateral post into the lateral port.

19. The process of claim 14, wherein the implanting step comprises the steps of:

inserting the femoral stem into a cavity in the prepared end of the femur bone;

impacting the femoral stem into the cavity.

20. The process of claim 14, further comprising the step of cleaning the lateral port and lateral hole after the drilling step to remove any bone debris.

\* \* \* \* \*